United States Patent [19]
Käsler et al.

[11] Patent Number: 5,976,844
[45] Date of Patent: Nov. 2, 1999

[54] RIBOFLAVIN-PRODUCTION PROCESS BY MEANS OF MICRO-ORGANISMS WITH MODIFIED ISOCITRATLYASE ACTIVITY

[75] Inventors: Bruno Käsler, Ludwigshafen; Hermann Sahm; Klaus-Peter Stahmann, both of Jülich; Georg Schmidt, Aldenhoven; Theo Böddecker, Jülich; Harald Seulberger, Dossenheim, all of Germany

[73] Assignee: BASF Aktiengesellschaft, Ludwigshafen, Germany

[21] Appl. No.: 08/981,690

[22] PCT Filed: Jul. 10, 1996

[86] PCT No.: PCT/EP96/03009

§ 371 Date: May 1, 1998

§ 102(e) Date: May 1, 1998

[87] PCT Pub. No.: WO97/03208

PCT Pub. Date: Jan. 30, 1997

[30] Foreign Application Priority Data

Jul. 13, 1995 [DE] Germany .................. 195 25 281
Dec. 5, 1995 [DE] Germany .................. 195 45 468

[51] Int. Cl.$^6$ .................. C12P 25/00; C12N 15/60; C12N 15/31
[52] U.S. Cl. .................. 435/118; 435/172.1; 435/232; 435/320.1; 530/23.2
[58] Field of Search .................. 435/118, 172.1, 435/232, 320.1; 530/23.2

[56] References Cited

U.S. PATENT DOCUMENTS 5,821,090  10/1998  Doval et al. .................. 435/88

FOREIGN PATENT DOCUMENTS 405 370   1/1991   European Pat. Off. .
93/03183  2/1993   WIPO .

OTHER PUBLICATIONS

Schmidt et al., Microbiology, Feb. 1, 1996, vol. 142, pp. 419–426).
Barth et al., Mol. Gen. Genet, May 1, 1993, vol. 241, pp, 422–430.
Bacher A, et al. Biochem Soc Trans. Feb, 1, 1996, vol. 24., No. 1, pp. 89–94.
Bacher A, et al. J Biol Chem., 1973, vol. 248. No. 17, pp. 6227–6231.
Mailander B, et al. J Biol Chem., Jun. 25, 1976 vol. 251, No. 12, pp. 3623–3628.
Penner D, et al. Biochim Biophys Acta., Nov. 28, 1967, No. 148, No. 2, pp. 481–485.
Mitsuda H, et al. Effects of various metabolites (sugars, carboxylic acids and alcohols) on riboflavin formation in non–growing cells of Ashbya gosspyii. J Nutr Sci Vitaminol (Tokyo). 1978;24(2):91–103.
Mitsuda H, et al. Nucleotide precursor in riboflavin biosynthesis. J Nutr Sci Vitaminol (Tokyo). 1976;22(6):477–80.
Mitsuda H, et al. Guanosine nucleotide precursor for flavinogenesis of Eremothecium Ashbyii. J Nutr Sci Vitaminol (Tokyo). 1975;21(5):331–45.
Mitsuda H, et al. The immediate nucleotide precursor, guanosine triphosphate, in the riboflavin biosynthetic pathway. J Nutr Sci Vitaminol (Tokyo). 1977;23(1):23–34.
Mitsuda H, et al Relationship between accumulation of guanine ribonucleotidyl–(3'–5')–adenosine and formation of riboflavin. J Nutr Sci Vitaminol (Tokyo). 1977;23(5):402–12.

*Primary Examiner*—Robert A. Wax
*Assistant Examiner*—Bradley S. Mayhew
*Attorney, Agent, or Firm*—Keil & Weinkauf

[57] ABSTRACT

The disclosure concerns a process for the microbial preparation of riboflavin by culturing riboflavin-producing microorganisms in a nutrient medium and then isolating the riboflavin which has been produced, which comprises using microorganisms in which the endogenous isocitrate lyase (ICL) activity has been altered.

11 Claims, 8 Drawing Sheets

Fragments of the Sau 3A-digestion after ultracentrifugation

RIBOFLAVIN-PRODUCTION PROCESS BY MEANS OF MICRO-ORGANISMS WITH MODIFIED ISOCITRATLYASE ACTIVITY

This application is a national stage application of PCT/EP96/03009, filed Jul. 10,1996.

The present invention relates to a process for preparing riboflavin using microorganisms having an altered isocitrate lyase activity.

Vitamin B$_2$, also termed riboflavin, is essential for humans and animals. Vitamin B$_2$ deficiency results in inflammation of the mucous membranes of the mouth and throat, cracks in the corners of the mouth, itching and inflammation in skin folds and similar skin damage, conjunctivitis, diminished visual acuity and clouding of the cornea. Cessation of growth and decrease in weight can occur in babies and children. Vitamin B$_2$ is therefore of particular economic importance as a vitamin preparation for use in vitamin deficiency and as a feed additive. In addition, it is also employed as a food dye, for example in mayonnaise, ice cream, desserts such as blancmange, etc.

Riboflavin is prepared either chemically or microbially. In the chemical methods of preparation, the riboflavin is usually obtained as a pure end product in multistep processes, with it being necessary to employ relatively expensive starting compounds such as D-ribose.

The preparation of riboflavin using microorganisms provides an alternative to the chemical preparation of this compound. Renewable raw materials, such as vegetable oils, can be employed as starting compounds for the microbial synthesis.

The preparation of riboflavin by means of fermenting fungi such as Ashbya gossypii or Eremothecium ashbyii has been disclosed (The Merck Index, Windholz et al., eds. Merck & Co., page 1183, 1983); however, yeasts, such as Candida or Saccharomyces, and bacteria, such as Clostridium, are also suitable for producing riboflavin. Bacterial strains which overproduce riboflavin are described, for example, in EP 405370, in which document the strains were obtained by transforming the riboflavin biosynthesis genes from *Bacillus subtilis*. However, these procaryotic genes are unsuitable for a recombinant method for preparing riboflavin which uses eucaryotes such as *Saccharomyces cerevisiae* or *Ashbya gossypii*.

WO 93/03183 describes the cloning of the riboflavin biosynthesis-specific genes from the eucaryotic organism *Saccharomyces cerevisiae*. These genes can be used to construct recombinant eucaryotic microorganisms which enable riboflavin to be produced efficiently.

Frequently, however, the starting compounds and substrates of the riboflavin biosynthesis enzymes are only present in limited quantity in the microorganism, so that no increase in riboflavin production is achieved despite increasing riboflavin biosynthesis activity.

It is therefore an object of the present invention to provide an improved microbial process for producing riboflavin, which process uses microorganisms which have no substrate limitation, or only relatively slight substrate limitation, and consequently enable riboflavin to be produced at an increased rate.

We have found that this object is achieved, according to the invention, by the endogenous isocitrate lyase activity of the microorganisms employed being altered. The alteration can be determined in relation to the unaltered starting strain. There are a large number of options for obtaining such microorganisms which have an altered ICL activity.

One option is to alter the endogenous ICL gene in such a way that it encodes an enzyme which has an increased ICL activity in relation to the starting enzyme. An increase in the activity of the enzyme can be achieved, for example, by increasing substrate turnover by means of altering the catalytic center, or by abolishing the effect of enzyme inhibitors. An increase in enzyme activity can also be brought about by increasing synthesis of the enzyme, for example by means of gene amplification or by means of eliminating factors which repress enzyme biosynthesis. The endogenous ICL activity is preferably increased by mutating the endogenous ICL gene. Mutations of this nature can be generated either in a random manner using standard methods, such as by using UV irradiation or mutation-inducing chemicals, or in a specific manner using genetic engineering methods such as deletions, insertions or substitutions.

Expression of the ICL gene is increased by increasing the copy number of the ICL gene and/or by reinforcing regulatory factors which have a positive effect on expression of the ICL gene. Thus, regulatory elements can preferably be reinforced at the level of transcription by using strong transcription signals such as promoters and enhancers. In addition, however, it is also possible to reinforce translation by, for example, improving the stability of the mRNA. In order to increase gene copy number, the ICL gene is incorporated into a gene construct or a vector which preferably contains regulatory gene sequences which are assigned to the ICL gene, in particular regulatory gene sequences which reinforce gene expression. A riboflavin-producing microorganism is then transformed with the gene construct containing the ICL gene.

The ICL gene is preferably isolated from microorganisms, in particular from the fungus *Ashbya gossypii*. However, all other organisms whose cells harbor the anaplerotic sequence of the glyoxylate cycle, and therefore isocitrate lyase, that is plants as well, are also suitable for isolating the gene. The gene can be isolated by homologous or heterologous complementation of a mutant which is defective in the ICL gene or else by heterologous probing or by PCR using heterologous primers. For the subcloning, the size of the insert in the complementing plasmid can then be reduced to a minimum by means of appropriate cutting with restriction enzymes. After the putative gene has been sequenced and identified, it is subcloned in a precisely fitting manner by means of fusion PCR. Plasmids which carry the resulting fragments as an insert are introduced into the ICL gene-defective mutant, which is then tested for the ability of the ICL gene to function. Finally, functional constructs are used to transform a riboflavin producer.

It is possible to obtain, after isolation and sequencing, isocitrate lyase genes which have nucleotide sequences which encode the aminoacid sequence given in SEQ ID NO:2 or its allelic variations. Allelic variations encompass, in particular, functional derivatives which can be obtained by deleting, inserting or substituting nucleotides from the sequence depicted in SEQ ID NO:1, while nevertheless retaining the ICL activity.

A promoter having the nucleotide sequence of nucleotides 176 to 550 of SEQ ID NO:1, or a DNA sequence having essentially the same effect, is, in particular, placed upstream of the isocitrate lyase genes. Thus, the promoter which is placed upstream of the gene can, for example, differ from the promoter having the given nucleotide sequence by means of one or more nucleotide replacements, or by means of (an) insertion(s) and/or (a) deletion(s), although the functional ability or effectiveness of the promoter is not impaired. Furthermore, the effectiveness of the promoter can be increased by altering its sequence, or the promoter can be completely replaced by more effective promoters.

Furthermore, regulatory gene sequences or regulator genes which, in particular, increase ICL gene activity can be assigned to the ICL gene. Thus, enhancers can be assigned to the ICL gene, which enhancers increase expression of the ICL gene by means of improving the interaction between the RNA polymerase and the DNA.

One or more DNA sequences can be placed upstream and/or downstream of the isocitrate lyase gene, with or without upstream promoter and/or with or without regulator gene, such that the isocitrate lyase gene is contained in a gene structure.

By means of cloning the ICL gene, it is possible to obtain plasmids or vectors which contain the ICL gene and which are suitable, as has already been mentioned above, for transforming a riboflavin producer. The cells which can be obtained by means of transformation, these cells preferably being transformed Ashbya gossypii cells, harbor the gene in replicatable form, ie. in additional copies on the chromosome, with the gene copies being integrated at any desired sites in the genome by means of homologous recombination, and/or on a plasmid or vector.

Another option for producing microorganisms which have an altered ICL activity is to produce microorganisms which exhibit resistance to substances which have an inhibitory effect on ICL and to select these microorganisms. Inhibitors of isocitrate lyase (ICL) are known to the skilled worker and are listed, for example, on page 291 of the Handbook of Enzyme Inhibitors, editor: Hellmut Zollner, Verlag Chemie, Weinheim, 1993. Particularly suitable inhibitors are phosphoenolpyruvate (PEP), 6-P-gluconate and maleate and, in particular, itaconate and oxalate.

If riboflavin-producing microorganism strains are then cultured in the presence of these inhibitors, it is found, surprisingly, that formation of the riboflavin is inhibited. On culture plates, this manifests itself in the formation of colonies which do not become yellow but instead remain white. When this system is used, therefore, strains which are resistant to inhibition of their isocitrate lyase are readily recognizable since these strains produce riboflavin even in the presence of inhibitor and therefore form yellow colonies. Strains of this nature can either arise by means of spontaneous mutation or can be produced by inducing appropriate mutations using customary methods such as chemical methods or UV irradiation. In this way, it is possible to obtain microorganism strains which secrete an increased quantity of riboflavin into the culture medium. The resistant strain having an increased formation of riboflavin which was in particular obtained was the Ashbya gossypii strain which was deposited in the DSM [German collection of microorganisms] under No. 10067.

Fungi are preferably employed as the microorganism in the novel process. Examples of suitable fungi are those which are listed in Table 6 on page 15 of Indian Chem Engr. Section B. Vol. 37, Nos. 1,2 (1995).

Those of the genera Pichia, Eremothetium and Ashbya, in particular Ashbya gossypii, are particularly suitable.

However, microorganisms other than fungi, for example bacteria, in particular the bacteria which are listed in Table 6 on page 16 of Indian Chem Engr. Section B. Vol. 37, Nos. 1,2 (1995), can also be employed.

BRIEF DESCRIPTION OF THE DRAWINGS

Table 1 identifies the individual steps for purification of ICL.

Table 2 shows the effects of various inhibitors on ICL activity.

EXAMPLE 1

Construction of a Genomic Library from Ashbya gossypii

Figure 4:
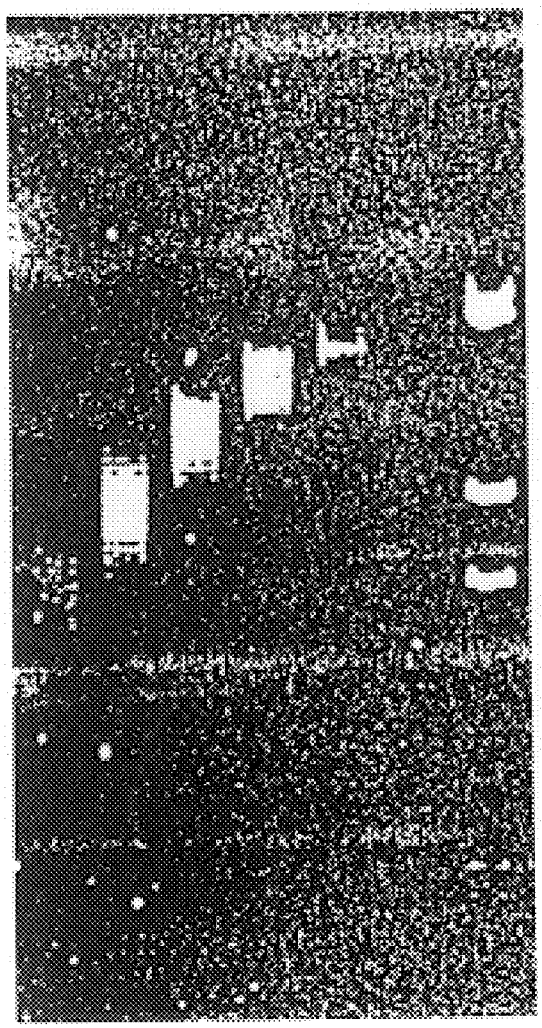
FIG. 4 shows a Ashbya gossypii genomic library partially digested with 3A.

The method of Wright and Philippsen (1991, Gene 109: 99–105) was used to isolate chromosomal DNA for the purpose of constructing a genomic DNA library. The DNA was partially digested with Sau 3A and then fractionated on a sucrose density gradient. The largest fragments (FIG. 4) were ligated to the Bam HI-cut E. coli/S. cerevisiae shuttle vector YEp 352 (J. E. Hill et al., 1993, Yeast 2: 163–167). E. coli DH5 a was transformed with this ligation mixture. 3600 colonies which were recognizable by their white color as being clones harboring insert-carrying plasmid were isolated from plates containing ampicillin and X-Gal. When thirty of these clones, which were chosen randomly, were investigated, it was found that they all did indeed harbor a plasmid, that these plasmids had inserts in a range of sizes between 7 and 18 kb and that all the inserts were different, as was evident from the restriction pattern. On the basis of the Ashbya gossypii genome having a size of $7 \times 10^3$ kb, there is a 97%–99.99% probability that every gene is present in this gene library. Every 100 clones were cultured in large streaks on an agar plate and the plasmids were subsequently prepared as a pool. The gene library consequently consisted of 36 plasmid pools.

EXAMPLE 2

Selection of the icl1-carrying gene library fragment

The plasmid preparations of the gene library were used to transform the yeast Saccharomyces cerevisiae ICL1d ura3 (fs) (E. Fernandez et al., 1992, Eur. J. Biochem. 204: 983–990). The ICL1 gene of this mutant is disrupted and the ura3 gene of the mutant has a mutation in its reading frame. As a result of having this genotype, the strain is unable to grow on ethanol as the carbon source and exhibits uracil auxotrophy. In the first step, the yeast cells which were transformed with the gene library were selected on minimal medium containing glucose as the sole carbon source. As a result of the ura3 gene being present on the plasmid, only those cells which had taken up a plasmid were able to grow since the minimal medium did not contain any uracil. 1900 clones were obtained in this step. These clones were transferred by replica plating to a minimal medium containing ethanol as the sole carbon source. Since isocitrate lyase, as an anaplerotic enzyme, is unconditionally required for growth on ethanol, only those clones which carried the ICL gene on the plasmid were able to grow. It was possible to isolate two clones which grew on ethanol.

EXAMPLE 3

Checking the Ability of the Isolated Gene Library Fragment to Function

In order to check whether the complementation of the chromosomal ICL defect was plasmid-encoded, the selected Saccharomyces clones were cultured twice on complete medium containing uracil and the resulting cells were grown as single colonies on plates. Out of 16 and 13, respectively, randomly chosen clones, 7 and 5, respectively, no longer grew on minimal medium containing glucose, and these same clones no longer grew on minimal medium containing ethanol, either. The curing of the plasmid therefore correlated with the loss of the ICL1d complementation.

The plasmid was reisolated from one of the two clones. It contained an insert of approximately 8 kb. Renewed transformation of the Saccharomyces mutant led to complementation of all the clones that were found. It was possible to use SphI to shorten the 8 kb fragment down to 2.9 kb, which were fully functional.

A specific isocitrate lyase activity of 0.3 U/mg of protein was found in a crude extract of the transformant which had grown on ethanol. In addition, a clear signal was obtained with a Western blot using polyclonal antibodies against the Ashbya ICL.

PCR using primers which were deduced from tryptic IECL peptides gave strong signals of the expected size. A two-dimensional electrophoresis gel was used to isolate a protein, which was decomposed into peptides with trypsin, with these peptides being sequenced terminally by means of Edman degradation. Comparison of the peptide sequences with databases gave more than 70% identity with *Saccharomyces cerevisiae* isocitrate lyase. Primers deduced from these sequences were used for the PCR. 3.3 kb of the approx. 8 kb-sized complementing gene library fragment were sequenced (Sanger et al. Proc. Natl. Acad. Sci. USA 74 (1977) 5463–5467). Database comparison resulted in two coding regions being found in the sequence which had been determined. One reading frame of 1680 bases (SEQ ID NO:1) exhibits 65% identity with the *Saccharomyces cerevisiae* ICL1 gene. The ICL gene is 375 bases upstream of a sequence which exhibits 84% identity with a Saccharomyces cerevisiae Ser-tRNA (SEQ ID NO:1).

Figure 5:
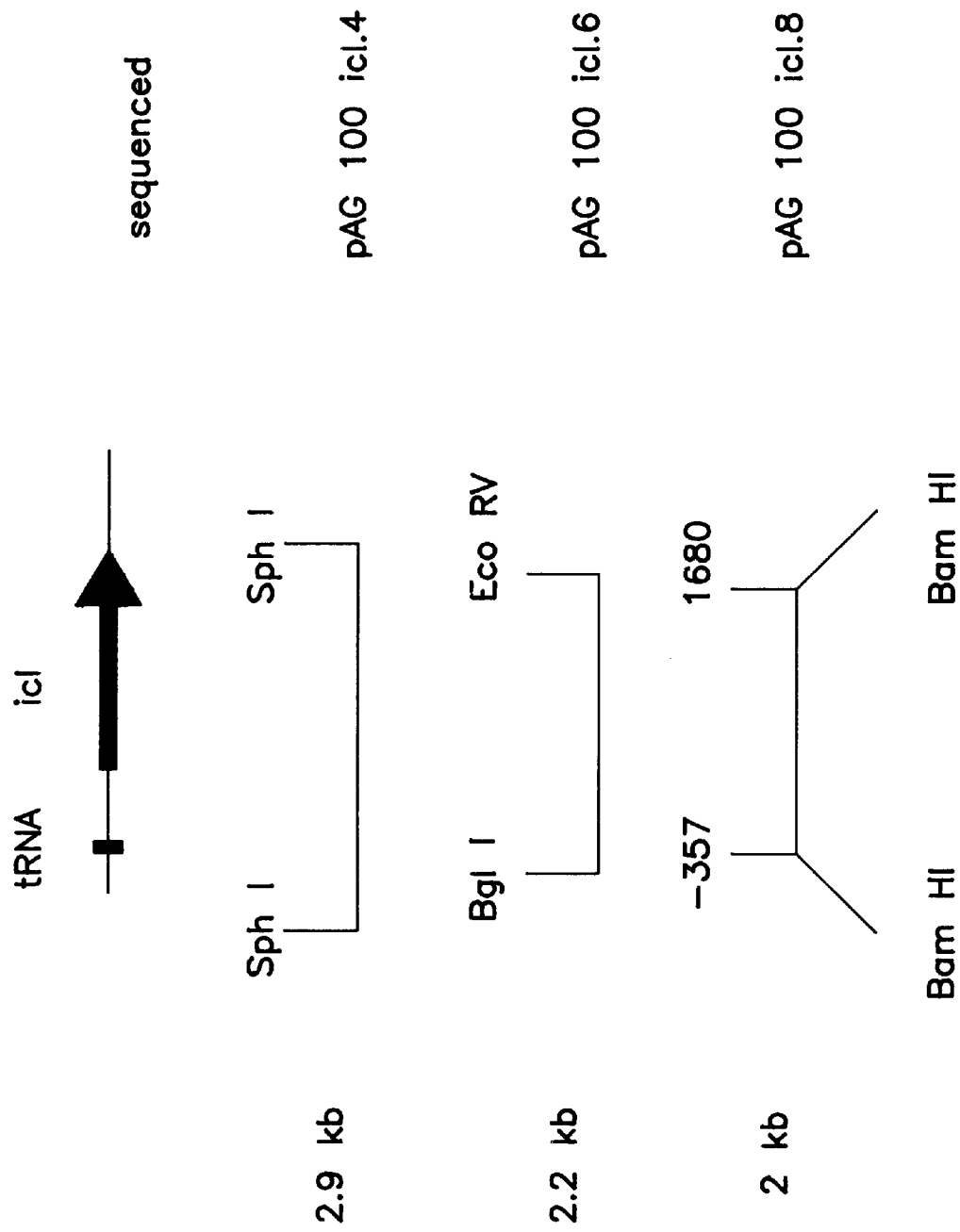
FIG. 5 shows fragments obtained by digestion of the Ashbya gossypii genomic library.
Figure 6:
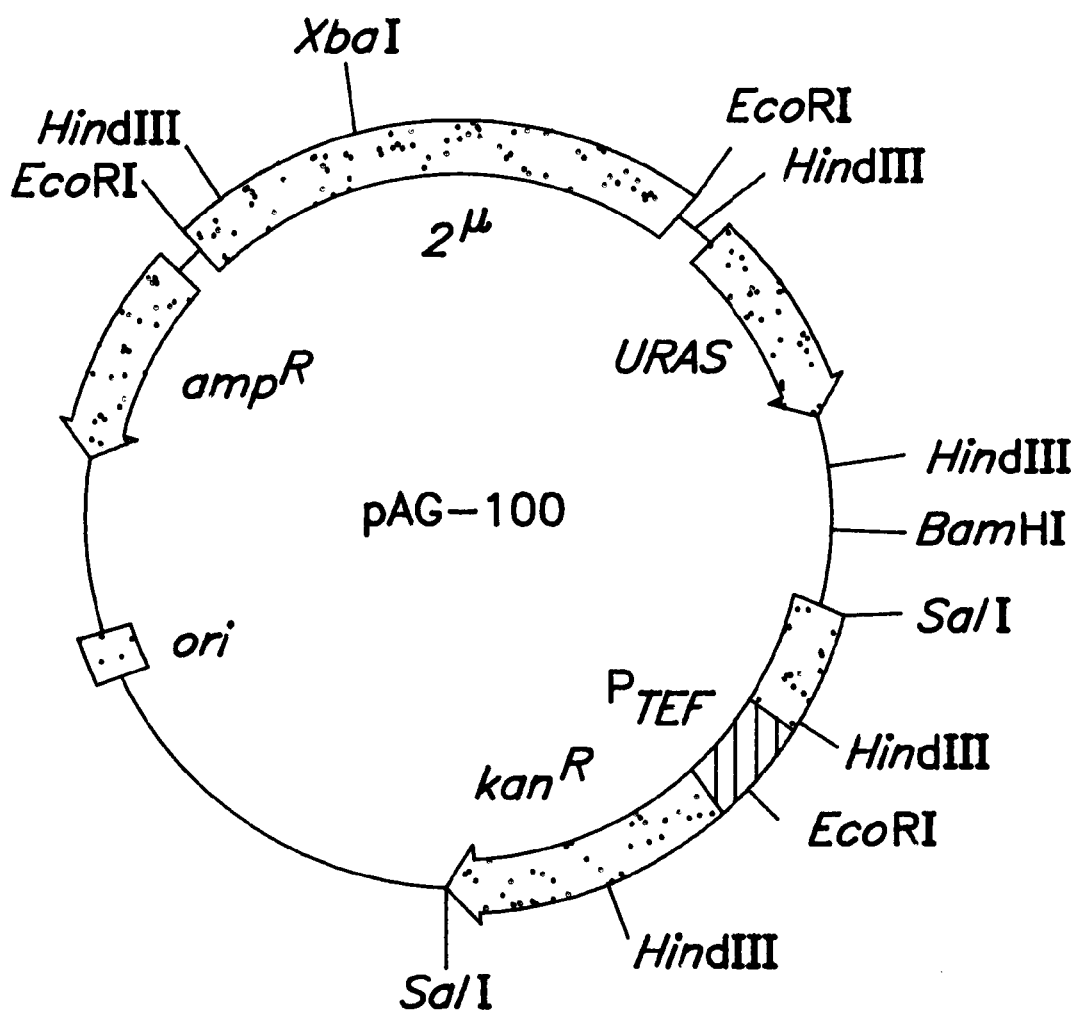
FIG. 6 shows a map of a pAG100 plasmid.

EXAMPLE 4
Ability of Subcloned ICL to Function in an *E. coli*/yeast/ Ashbya Shuttle Vector Two fragment obtained by restriction digestion and a PCR product of the isolated gene library fragment (FIG. 5) were cloned into the pAG 100 plasmid (FIG. 6), which was constructed by Steiner and Philippsen (1994, Mol. Gen. Genet 242: 263–271). The fragments were a 2.9 kb Sph I fragment (pAG 100 icl.4) and a 2.2 kb Bgl I/Eco RV fragment (pAG 100 icl.6). Both fragments contained the Ser-tRNA. For this reason, a PCR amplification of the putative gene together with fused-on Bam HI cleavage sites (pAG 100 icl.8) was carried out in addition. All three DNAs were cloned into the Bam HI site of the pAG 100 plasmid. The yeast mutant Saccharomyces cerevisiae ICL1d ura3 (fs) was transformed with the resulting plasmids. All three constructs complemented the ICLId disruption completely, ie. carried functional genes.

EXAMPLE 5
Effect of the ICL-carrying Plasmids on Riboflavin Formation by *Ashbya gossypii*

Figure 7:
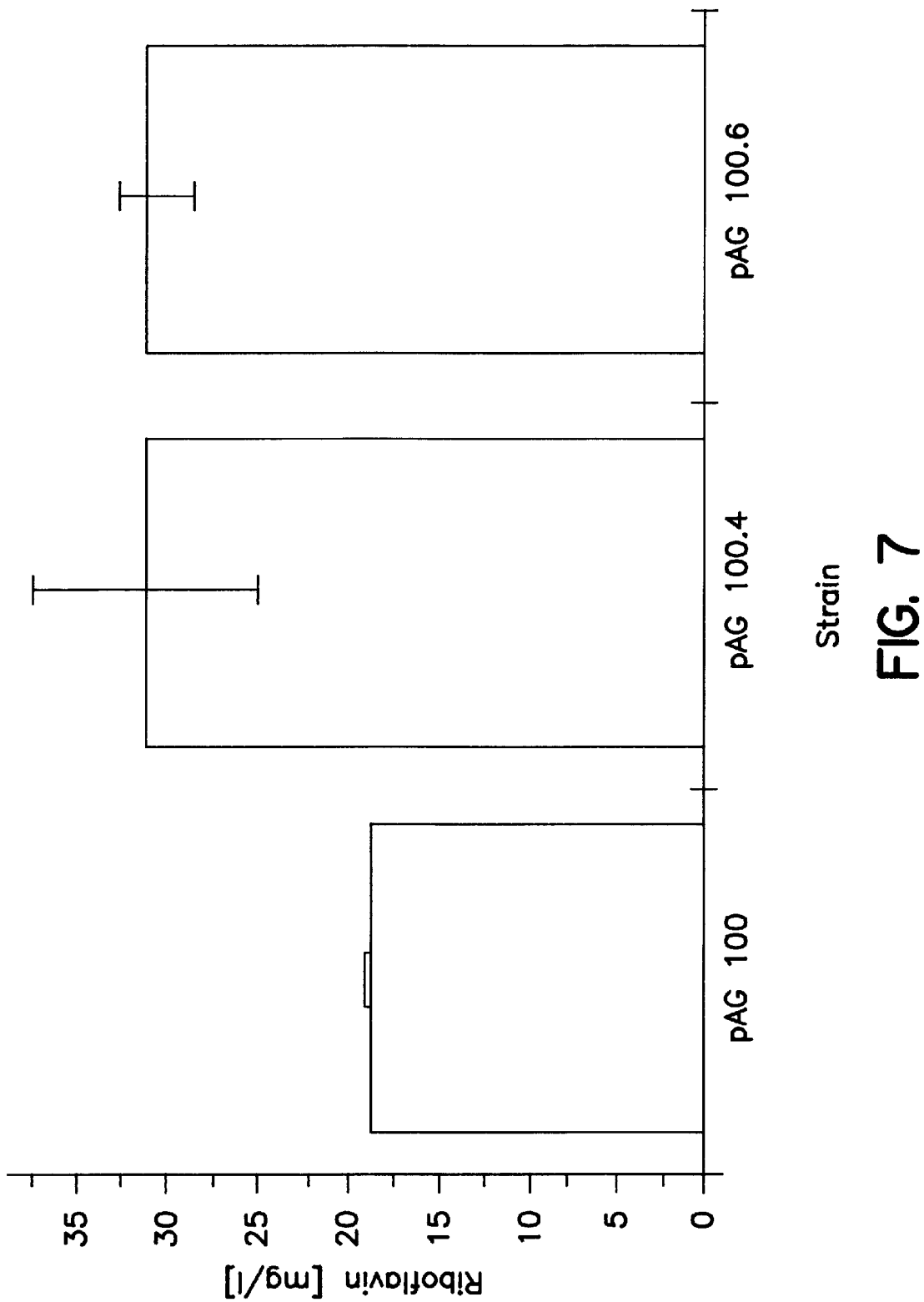
FIG. 7 shows the formation of riboflavin by Ashbya gossypii 100, Ashbya gossypii 100.4 and Ashbya gossypii 100.6.
Figure 8:
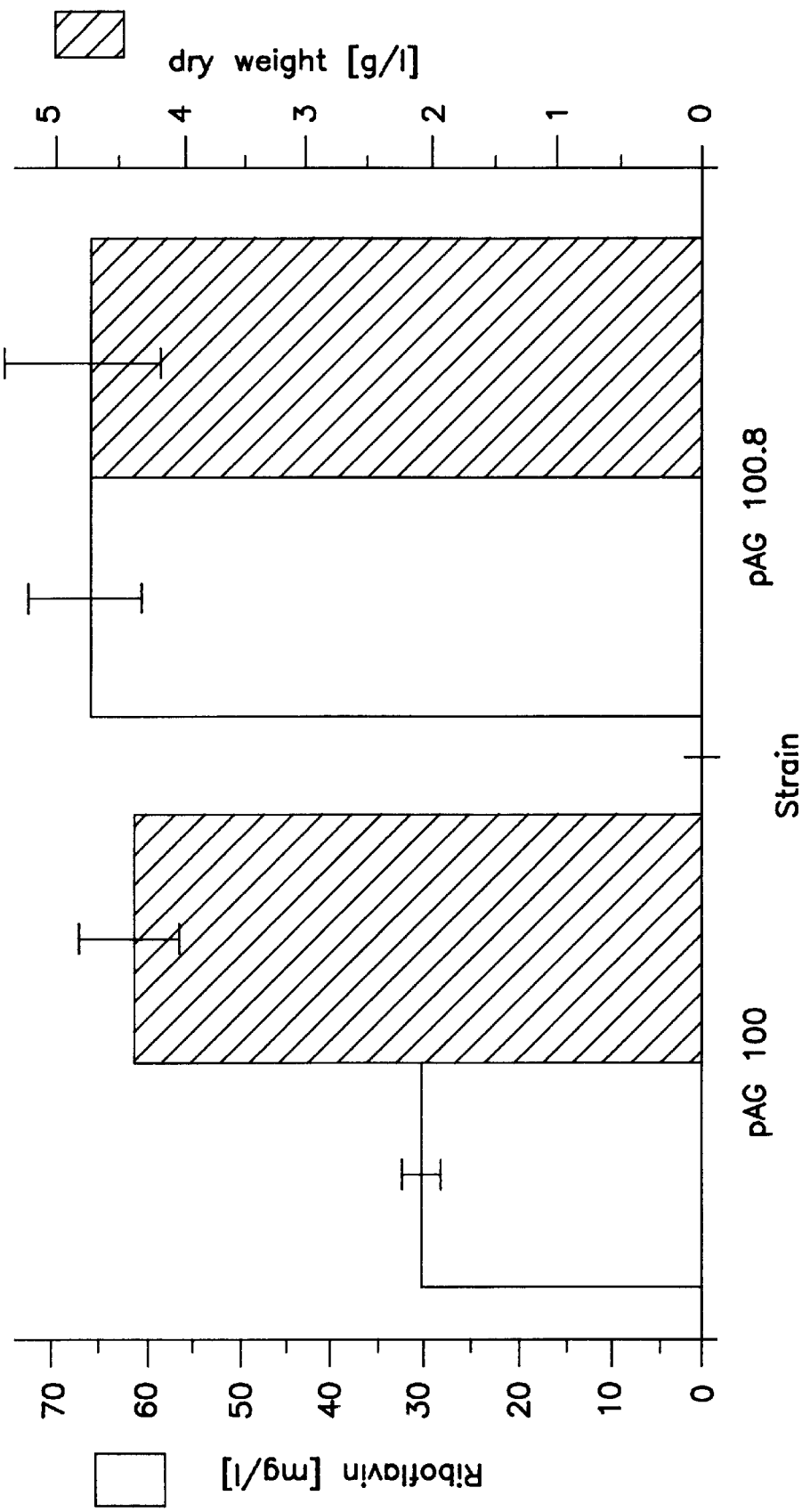
FIG. 8 shows the formation of riboflavin by Ashbya gossypii 100 and Ashbya gossypii 100.8.

Transformation of *Ashbya gossypii* (method: Wright and Philippsen, 1991, Gene 109: 99–105) with the above-described plasmids led to significant increases in riboflavin formation. These strains were cultured in 500 ml shaking flasks which were equipped with two baffles and which each contained 50 ml of medium comprising 10 g/l soya bean oil, 10 g/l yeast extract and 200 μg/ml Geneticin. The control strain A. gossypii pAG 100, which harbored a plasmid without any insert, produced 18.7±0.1 mg/l riboflavin in two days. The strains *A. gossypii* pAG 100.4 and *A. gossypii* pAG 100.6 produced 31.2±6.1 mg/l and 31.0±2.0 mg/l riboflavin, respectively (FIG. 7). Due to the high degree of variability, it was not possible to measure any significant change in the specific activity of the isocitrate lyase. In a medium which was also supplemented with 3 g/l glycine, the strain *A. gossypii* pAG 100.8 produced 65±5.6 mg/l riboflavin over a period of three days. By contrast, in a direct comparison, the control strain *A. gossypii* pAG 100 only formed 29.9±1.8 mg/l riboflavin (FIG. 8). It was not possible to measure significant differences either in isocitrate lyase specific activity or in mycelium dry weight.

EXAMPLE 6
Purification of an Isocitrate Lyase (ICL)

In order to identify substances exerting an inhibitory effect on ICL, the *Ashbya gossypii* ICL was first of all purified. The enzyme was isolated and purified after the fungal mycelium had been grown on vegetable oil. The individual purification steps are summarized in Table 1: as can be seen from this table, a typical crude extract, which was prepared from approx. 25 g of mycelium and which was obtained by means of cell disruption using a French Press, contains 220 units of ICL activity. Approximately 78% of this activity is recovered in dissolved form in the supernatant after centrifuging at 40,000 g. Subsequent fractionation by means of ammonium sulfate precipitation results in a three-fold enrichment of the enzyme. After gel filtration through a Sephacryl S-300 column, the ICL is bound to the cation exchange material Mono S-Sepharose and eluted with NaCl. The resulting preparation is homogeneous by SDS polyacrylamide gel electrophoresis and has a specific activity of 18.4 U/mg.

EXAMPLE 7
Identification of ICL Inhibitors

Figure 1:
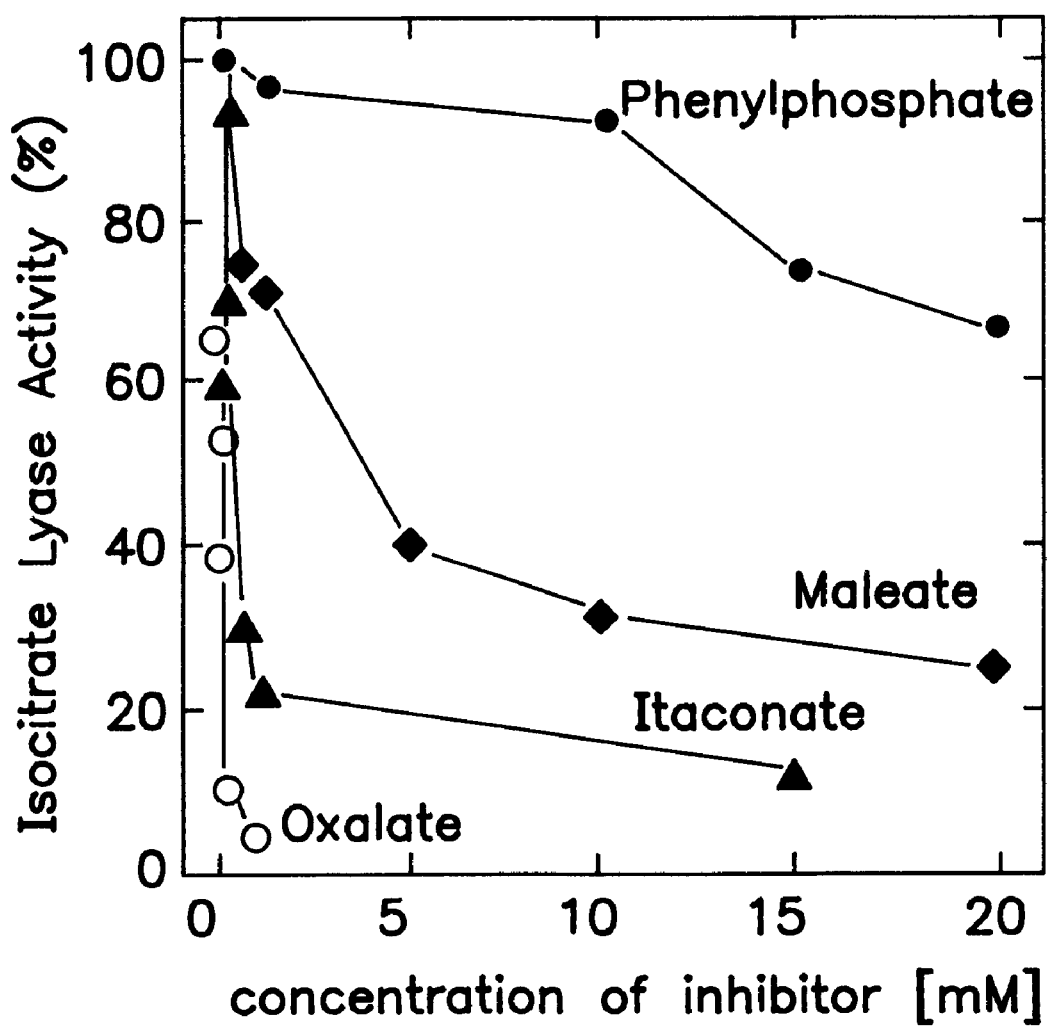
FIG. 1 shows the effects of various inhibitors on ICL activity.

The purified enzyme can be used to measure the effects of substances on its activity in a calorimetric test (Dixon, H. and Kornberg, H. L. (1959), Biochem. J. 72, 3: Assay methods for key enzymes of the glyoxylate cycle). The effects of the tested substances on the enzyme are summarized and depicted in Table 2 and FIG. 1, respectively. Substances to be investigated included those which, as metabolites in the fungal cell, could have an inhibitory effect on the enzyme. Of these, 6-P-gluconate and phosphoenolpyruvate exhibited the most marked inhibitory effects, giving inhibitions of greater than 50% at a concentration of 10 mM. However, itaconate and oxalate, which presumably do not participate in the metabolism of the fungus, exhibited substantially greater effects. A concentration of just 1 mM resulted in 78% inhibition and 95% inhibition, respectively.

EXAMPLE 8
Characterization of an Itaconate-selected Mutant

Figure 2:
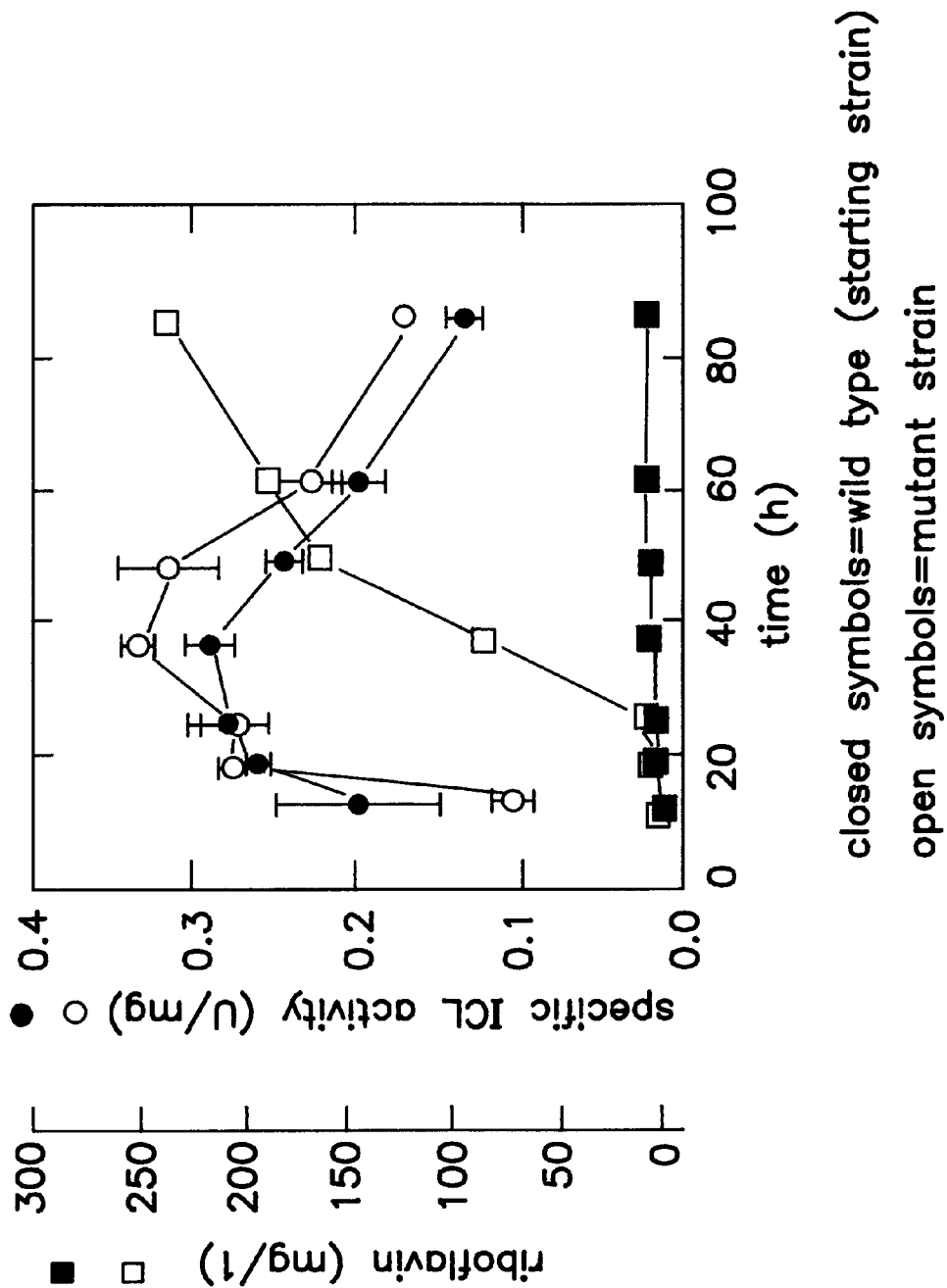
FIG. 2 compares riboflavin production in wild-type and mutant strains.

Mutations in the hereditary material of isolated spores of the fungus can be produced by irradiating the spores with UV light. When a radiation dose at which 10–20% of the spores survive is used, mutants which are resistant to inhibition of riboflavin formation by itaconate are obtained. When a mutant which has been isolated in this way is grown on soya bean oil, it exhibits a formation of riboflavin which is 25 times greater than that of the starting strain (FIG. 2). The specific activity of the ICL is increased by up to 15% during the phase of riboflavin formation (FIG. 2). Using antibodies, it can be demonstrated that the protein quantity is increased. The ICL from the mutant exhibits the same behavior with regard to inhibition by itaconate as does the starting strain

EXAMPLE 9
Correlation of Riboflavin Formation and Specific ICL Activity

Figure 3:
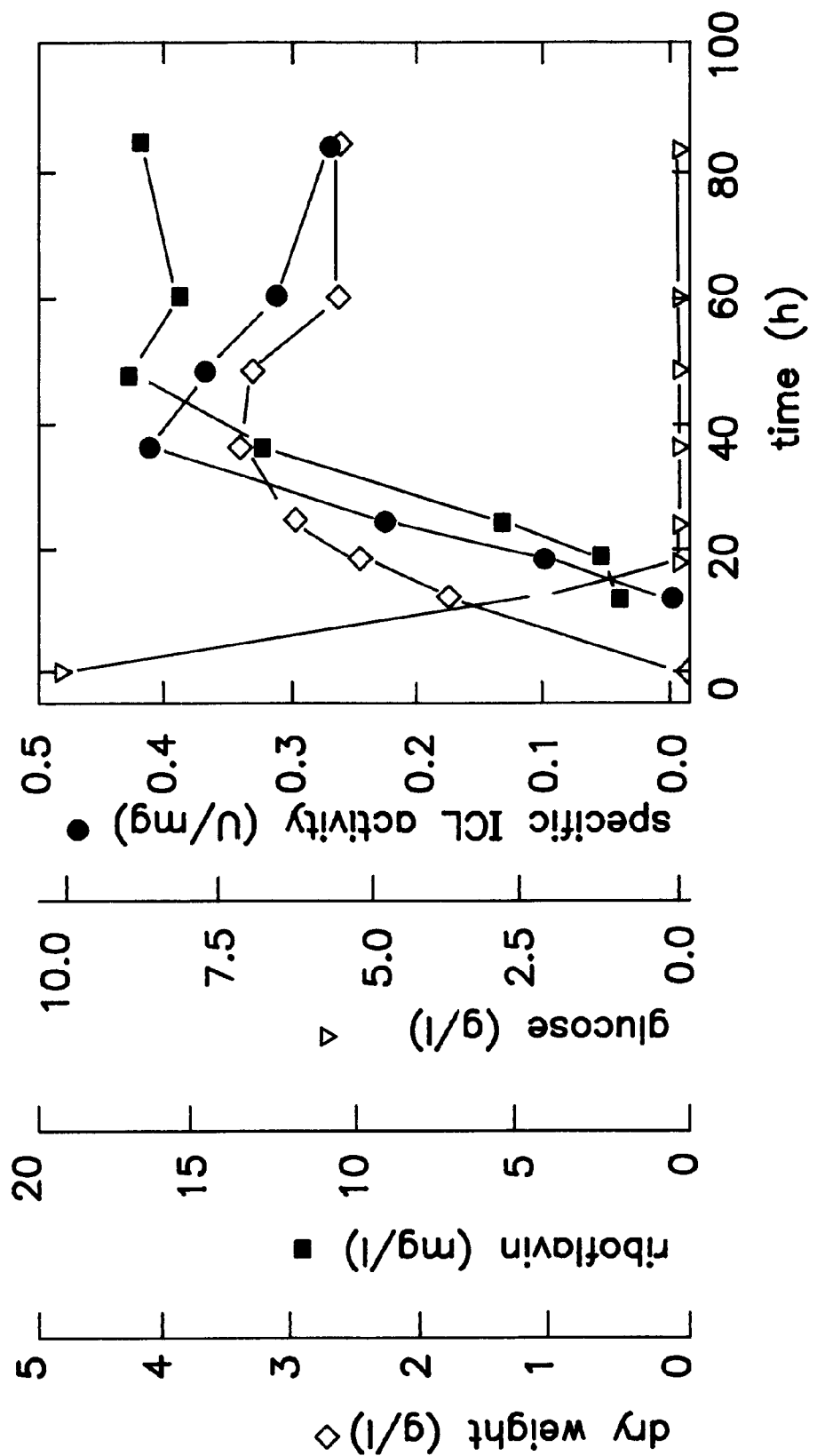
FIG. 3 shows ICL activity, riboflavin formation and glucose concentration as a function of time.

A surprising indication that there is a causal relationship between ICL and riboflavin formation is provided by the observation that, when glucose is offered as a substrate, the fungus only begins to produce riboflavin after the glucose has been consumed. It is precisely then that the ICL, which has previously be repressed by the glucose, also becomes measurable in the crude extract and increases up to activities such as are found when the fungus is growing on oil (FIG. 3).

We claim:

1. A process for the microbial preparation of riboflavin, comprising culturing in a nutrient medium a microorganism that has been genetically altered to exhibit increased isocitrate lvase (ICL) activity and isolating the riboflavin that has been produced.

2. A process as defined in claim 1 wherein the genetically altered microorganism expresses an ICL enzyme that has higher specific activity than the ICL enzyme of the non-genetically altered microorganism due to an alteration in the ICL gene.

3. A process as defined in claim 1, wherein the genetically altered microorganism expresses ICL enzyme at a higher level than is expressed in the non-aseptically altered microorganism due to increased copy number of the ICL gene.

4. A process as defined in claim 1, wherein the genetically altered microorganism expresses ICL enzyme at a higher level than is expressed in the non-genetically altered microorganism due to alteration in the sequences that regulate ICL gene expression.

5. A process as defined in claim 1, wherein the genetically altered microorganism expresses ICL that is more resistant to feedback inhibition than the non-genetically altered microorganism due to a mutation in the ICL gene.

6. A process as defined in claim 5, wherein the microorganisms are resistant to the substances itaconate and oxalate.

7. A process as defined claim 1, wherein a fungus is used as the microorganism.

8. A process as defined in claim 7, wherein a fungus from the Ashbya genus is used.

9. An isolated and purified polynucleotide encoding the amino acid sequence depicted in SEQ ID NO:2.

10. A polynucleotide construct comprising the polynucleotide of claim 9.

11. A polynucleotide construct as claimed 10, wherein the polynucleotide encoding the amino acid sequence depicted in SEQ ID NO:2 has been functionally linked to one more regulatory signals for the purpose of increasing expression.

* * * * *

UNITED STATES PATENT AND TRADEMARK OFFICE
CERTIFICATE OF CORRECTION

PATENT NO. : 5,976,844
DATED : November 2, 1999
INVENTOR(S) : KAESLER et al.

It is certified that error appears in the above-identified patent and that said Letters Patent is hereby corrected as shown below:

Col. 15, claim 1, line 17, "lvase" should be --lyase--.

Col. 15, claim 3, line 25, "non-aseptically" should be --non-genetically--.

Col. 16, claim 11, line 26, after "claimed" insert --in claim--.

Col. 16, claim 11, line 28, after "one" insert --or--.

Signed and Sealed this

Twenty-ninth Day of August, 2000

Attest:

Q. TODD DICKINSON

Attesting Officer

Director of Patents and Trademarks

```
                            SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 2364 base pairs
        (B) TYPE: Nucleic acid
        (C) STRANDEDNESS: double
        (D) TOPOLOGY: linear (ii) MOLECULE TYPE: cDNA to mRNA (iii) HYPOTHETICAL: NO (iii) ANTI-SENSE: NO (ix) FEATURE:
        (A) NAME/KEY: 5'UTR
        (B) LOCATION: 1..550

(ix) FEATURE:
        (A) NAME/KEY: CDS
        (B) LOCATION: 551..2233

(ix) FEATURE:
        (A) NAME/KEY: 3'UTR
        (B) LOCATION: 2234..2364

(xi) SEQUENCE DESCRIPTION: SEQ ID NO: 1:

CGAAAGCGCC AAATACCGGA AACGGCACAG GCGCAGCTCT AATAGCCGTT CCACGATAAC      60

TTTGGAAGTT ATGGCACTAT GGCCGAGTGG TTAAGGCGAC AGACTTGAAA TCTGTTGGGC     120

TCTGCCCGCG CTGGTTCAAA TCCTGCTGGT GTCGTTATTT TTGCCGTTTC TTTTTAGATG     180

AAACTCAGGG GCCTTTAGTC CGCCCTTTTG CCCGCTGATT CATCGCCCGC CAGCAACACC     240

GGTTGAGCCG ATCAGCGCAA GAACGCGCAA AGTCACGTAT GGCCCCTAAG AGTTGAGCTC     300

TCCCCCTCGG CTCCTTCCGG GCGCGGAAAA GCCTGCGTCA CCCCATTAAG TCCGAAACCG     360

CGTTCAAGTG TACTTGGTCC GGGCCAATGT GGTTGCCTCA TCCGAGTCAC CGATACGCAG     420

GTGCGCCCGT CGAGTCACCA TTAGGAGTAG AGCATCTGAT TATATATAGG CCTAGTTACA     480

GCGGTAACAT AGACTGATAG CTCCAGCTCC AGCACTAGCT TGTAGGACAT CTGCGCGACA     540

CCCAGTGAAC ATG TCC CCT TCC GTC AGA GAC GCC CGC AAC GAC CTT GCC       589
            Met Ser Pro Ser Val Arg Asp Ala Arg Asn Asp Leu Ala
              1               5                  10

AGC CTG CAA CAG CAG GCA GCC GCC GAA GCC GAG GAT ATT AGG AGA TGG      637
Ser Leu Gln Gln Gln Ala Ala Ala Glu Ala Glu Asp Ile Arg Arg Trp
    15                  20                  25

TGG AGC CAG CCA CGG TGG GCG GGC ACC AAG CGC GTG TAC ACG GCC GAG      685
Trp Ser Gln Pro Arg Trp Ala Gly Thr Lys Arg Val Tyr Thr Ala Glu
30                  35                  40                  45

GAC ATC GTC AAG CGC CGC GGC ACG TTC CCT GTC GTC GAA TAC CCA TCT      733
Asp Ile Val Lys Arg Arg Gly Thr Phe Pro Val Val Glu Tyr Pro Ser
                50                  55                  60
```

-continued

| | |
|---|---|
| TCC GTA ATG GCG GAC AAG CTC GTG GAG ACA TTG GCG CGG CAC TCG CGC<br>Ser Val Met Ala Asp Lys Leu Val Glu Thr Leu Ala Arg His Ser Arg<br>              65                    70                   75 | 781 |
| AAC GGC ACG GTT TCA CAG ACG TTC GGA GTG CTC GAC CCA GTG CAA ATG<br>Asn Gly Thr Val Ser Gln Thr Phe Gly Val Leu Asp Pro Val Gln Met<br>        80                    85                    90 | 829 |
| ACG CAA ATG GTG AAG TAT CTG GAC ACG ATT TAC GTG TCT GGC TGG CAA<br>Thr Gln Met Val Lys Tyr Leu Asp Thr Ile Tyr Val Ser Gly Trp Gln<br> 95                    100                  105 | 877 |
| TGC AGC GCC ACG GCT TCG ACC TCG AAC GAG CCT GGG CCC GAT CTC GCG<br>Cys Ser Ala Thr Ala Ser Thr Ser Asn Glu Pro Gly Pro Asp Leu Ala<br>110                  115                  120                 125 | 925 |
| GAC TAT CCG ATG GAC ACC GTG CCA AAC AAG GTC GAG CAC CTG TTC ATG<br>Asp Tyr Pro Met Asp Thr Val Pro Asn Lys Val Glu His Leu Phe Met<br>             130                  135                 140 | 973 |
| GCG CAG CTG TTC CAC GAC CGG AAA CAG CGC GAG GCC CGC CTG TCG TGC<br>Ala Gln Leu Phe His Asp Arg Lys Gln Arg Glu Ala Arg Leu Ser Cys<br>             145                  150                 155 | 1021 |
| ACT ACC CAG CGC GAG CTC GAC CAA TTG GGG CCT GAG ATT GAC TAC TTG<br>Thr Thr Gln Arg Glu Leu Asp Gln Leu Gly Pro Glu Ile Asp Tyr Leu<br>        160                    165                    170 | 1069 |
| AGG CCG ATT GTC GCT GAC GCA GAC ACC GGC CAC GGC GGG CTA ACA GCC<br>Arg Pro Ile Val Ala Asp Ala Asp Thr Gly His Gly Gly Leu Thr Ala<br>175                  180                  185 | 1117 |
| GTC TTT AAA CTC ACG AAG ATG TTC ATC GAG CGC GGT GCA GCC GGT ATC<br>Val Phe Lys Leu Thr Lys Met Phe Ile Glu Arg Gly Ala Ala Gly Ile<br>190                  195                  200                 205 | 1165 |
| CAC ATG GAG GAC CAG TCC TCC AGC AAC AAA AAG TGC GGG CAC ATG GCG<br>His Met Glu Asp Gln Ser Ser Ser Asn Lys Lys Cys Gly His Met Ala<br>             210                  215                 220 | 1213 |
| GGC CGC TGC GTG ATC CCT GTT CAG GAG CAC ATT AGT CGT TTA GTG ACT<br>Gly Arg Cys Val Ile Pro Val Gln Glu His Ile Ser Arg Leu Val Thr<br>             225                  230                 235 | 1261 |
| GTG CGC ATG TGT GCG GAC GTG ATG CAC TCG AAC CTG GTG CTT GTC GCG<br>Val Arg Met Cys Ala Asp Val Met His Ser Asn Leu Val Leu Val Ala<br>        240                    245                    250 | 1309 |
| AGA ACA GAC TCG GAG GCC GCC ACC TTA CTT AGC TCG AAC ATT GAC GCG<br>Arg Thr Asp Ser Glu Ala Ala Thr Leu Leu Ser Ser Asn Ile Asp Ala<br>255                  260                  265 | 1357 |
| CGC GAT CAT TAC TAC ATT GTC GGG GCC TCG AAC CCT GAG GTA ACT GTA<br>Arg Asp His Tyr Tyr Ile Val Gly Ala Ser Asn Pro Glu Val Thr Val<br>270                  275                  280                 285 | 1405 |
| CCG CTG ATC GAA GTT TTG GAC GCC GCG CAG CAG GCC GGC GCC TCA GGT<br>Pro Leu Ile Glu Val Leu Asp Ala Ala Gln Gln Ala Gly Ala Ser Gly<br>             290                  295                 300 | 1453 |
| GAC AGA TTG GCT CAG CTA GAG GAG GAC TGG TGC AAG AAG GCC AAG TTG<br>Asp Arg Leu Ala Gln Leu Glu Glu Asp Trp Cys Lys Lys Ala Lys Leu<br>             305                  310                 315 | 1501 |
| AGG CTC TTC CAC GAG GCA TTT GCC GAC CAG GTG AAT GCC AGC CCT TCG<br>Arg Leu Phe His Glu Ala Phe Ala Asp Gln Val Asn Ala Ser Pro Ser<br>        320                    325                 330 | 1549 |
| ATC AAA GAC AAG GCG GGC GTT ATT GCC AAA TTT AAC TCA CAG ATC GGG<br>Ile Lys Asp Lys Ala Gly Val Ile Ala Lys Phe Asn Ser Gln Ile Gly<br>335                  340                  345 | 1597 |
| CCA CAG ACA GGC GCG TCG ATC AGA GAG ATG CGC AAA CTG GGC CGC GAG<br>Pro Gln Thr Gly Ala Ser Ile Arg Glu Met Arg Lys Leu Gly Arg Glu<br>350                  355                  360                 365 | 1645 |
| CTG CTC GGG CAG GAC GTC TAC TTC GAC TGG GAC CTG CCT CGC GCT AGA<br>Leu Leu Gly Gln Asp Val Tyr Phe Asp Trp Asp Leu Pro Arg Ala Arg<br>             370                  375                 380 | 1693 |

```
GAG GGC TTG TAC CGC TAC AAG GGC GGC ACC CAG TGC GCG ATC ATG CGC    1741
Glu Gly Leu Tyr Arg Tyr Lys Gly Gly Thr Gln Cys Ala Ile Met Arg
            385                 390                 395

GCA CGC GCG TTC GCG CCG TAC GCC GAC CTG GTC TGG TTC GAA TCC AAC    1789
Ala Arg Ala Phe Ala Pro Tyr Ala Asp Leu Val Trp Phe Glu Ser Asn
            400                 405                 410

TTC CCT GAC TTC CAG CAG GCT AAG GAG TTT GCG CAG GGC GTG CGC GAG    1837
Phe Pro Asp Phe Gln Gln Ala Lys Glu Phe Ala Gln Gly Val Arg Glu
            415                 420                 425

AAG TTC CCC AAC AAG TGG ATG GCC TAC AAC TTG TCG CCC AGC TTC AAC    1885
Lys Phe Pro Asn Lys Trp Met Ala Tyr Asn Leu Ser Pro Ser Phe Asn
430                 435                 440                 445

TGG CCG AAG GCC ATG CCT CCC AAG GAG CAG GAG AAC TAC ATC CAA CGG    1933
Trp Pro Lys Ala Met Pro Pro Lys Glu Gln Glu Asn Tyr Ile Gln Arg
                450                 455                 460

CTG GGC GAG ATC GGA TAT GTG TGG CAG TTC ATC ACG CTA GCC GGC CTG    1981
Leu Gly Glu Ile Gly Tyr Val Trp Gln Phe Ile Thr Leu Ala Gly Leu
                465                 470                 475

CAT ACC AAT GCC TTG GCC ATC GAC AAC TTC TCG CGC GAA TTC AGC AGG    2029
His Thr Asn Ala Leu Ala Ile Asp Asn Phe Ser Arg Glu Phe Ser Arg
                480                 485                 490

TTC GGA ATG CGT GCG TAT GCA CAA GGC ATC CAG CAG AGG GAG ATG GAC    2077
Phe Gly Met Arg Ala Tyr Ala Gln Gly Ile Gln Gln Arg Glu Met Asp
            495                 500                 505

GAG GGC GTC GAT GTC CTA AAA CAC CAG AAG TGG GCC GGC GCA GAG TAT    2125
Glu Gly Val Asp Val Leu Lys His Gln Lys Trp Ala Gly Ala Glu Tyr
510                 515                 520                 525

GTT GAC AGC ATT CTC AAG CTT GCC CAG GGC GGT GTG TCT TCG ACA GCC    2173
Val Asp Ser Ile Leu Lys Leu Ala Gln Gly Gly Val Ser Ser Thr Ala
                530                 535                 540

TCG ATG GGT AAG GGT GTA ACC GAA GAG CAG TTC GGC TCC TCA AAC GGT    2221
Ser Met Gly Lys Gly Val Thr Glu Glu Gln Phe Gly Ser Ser Asn Gly
            545                 550                 555

GCC AAA CTA TGATATCATC TCTGAGTCAT TTCTCTCGAC AAGATCCTCG            2270
Ala Lys Leu
        560

GCCAGACTTC TGGAATATAT ATAACATCGG GTACCCCGAC ATCCCTGCCT TCCGCAACGT    2330

GCGAAGCAGC TGATACGTAT ACTTTAAACG CACA                                2364

(2) INFORMATION FOR SEQ ID NO: 2:

(i) SEQUENCE CHARACTERISTICS:
         (A) LENGTH: 560 amino acids
         (B) TYPE: amino acid
         (D) TOPOLOGY: linear (ii) MOLECULE TYPE: protein (xi) SEQUENCE DESCRIPTION: SEQ ID NO: 2:

Met Ser Pro Ser Val Arg Asp Ala Arg Asn Asp Leu Ala Ser Leu Gln
 1               5                  10                  15

Gln Gln Ala Ala Ala Glu Ala Glu Asp Ile Arg Arg Trp Trp Ser Gln
                20                  25                  30

Pro Arg Trp Ala Gly Thr Lys Arg Val Tyr Thr Ala Glu Asp Ile Val
            35                  40                  45

Lys Arg Gly Thr Phe Pro Val Val Glu Tyr Pro Ser Ser Val Met
     50                  55                  60

Ala Asp Lys Leu Val Glu Thr Leu Ala Arg His Ser Arg Asn Gly Thr
65                  70                  75                  80
```

-continued

```
Val Ser Gln Thr Phe Gly Val Leu Asp Pro Val Gln Met Thr Gln Met
                 85                  90                  95

Val Lys Tyr Leu Asp Thr Ile Tyr Val Ser Gly Trp Gln Cys Ser Ala
            100                 105                 110

Thr Ala Ser Thr Ser Asn Glu Pro Gly Pro Asp Leu Ala Asp Tyr Pro
            115                 120                 125

Met Asp Thr Val Pro Asn Lys Val Glu His Leu Phe Met Ala Gln Leu
        130                 135                 140

Phe His Asp Arg Lys Gln Arg Glu Ala Arg Leu Ser Cys Thr Thr Gln
145                 150                 155                 160

Arg Glu Leu Asp Gln Leu Gly Pro Glu Ile Asp Tyr Leu Arg Pro Ile
                165                 170                 175

Val Ala Asp Ala Asp Thr Gly His Gly Gly Leu Thr Ala Val Phe Lys
            180                 185                 190

Leu Thr Lys Met Phe Ile Glu Arg Gly Ala Ala Gly Ile His Met Glu
        195                 200                 205

Asp Gln Ser Ser Ser Asn Lys Lys Cys Gly His Met Ala Gly Arg Cys
    210                 215                 220

Val Ile Pro Val Gln Glu His Ile Ser Arg Leu Val Thr Val Arg Met
225                 230                 235                 240

Cys Ala Asp Val Met His Ser Asn Leu Val Leu Val Ala Arg Thr Asp
                245                 250                 255

Ser Glu Ala Ala Thr Leu Leu Ser Ser Asn Ile Asp Ala Arg Asp His
            260                 265                 270

Tyr Tyr Ile Val Gly Ala Ser Asn Pro Glu Val Thr Val Pro Leu Ile
        275                 280                 285

Glu Val Leu Asp Ala Ala Gln Gln Ala Gly Ala Ser Gly Asp Arg Leu
    290                 295                 300

Ala Gln Leu Glu Glu Asp Trp Cys Lys Lys Ala Lys Leu Arg Leu Phe
305                 310                 315                 320

His Glu Ala Phe Ala Asp Gln Val Asn Ala Ser Pro Ser Ile Lys Asp
                325                 330                 335

Lys Ala Gly Val Ile Ala Lys Phe Asn Ser Gln Ile Gly Pro Gln Thr
            340                 345                 350

Gly Ala Ser Ile Arg Glu Met Arg Lys Leu Gly Arg Glu Leu Leu Gly
        355                 360                 365

Gln Asp Val Tyr Phe Asp Trp Asp Leu Pro Arg Ala Arg Glu Gly Leu
    370                 375                 380

Tyr Arg Tyr Lys Gly Gly Thr Gln Cys Ala Ile Met Arg Ala Arg Ala
385                 390                 395                 400

Phe Ala Pro Tyr Ala Asp Leu Val Trp Phe Glu Ser Asn Phe Pro Asp
                405                 410                 415

Phe Gln Gln Ala Lys Glu Phe Ala Gln Gly Val Arg Glu Lys Phe Pro
            420                 425                 430

Asn Lys Trp Met Ala Tyr Asn Leu Ser Pro Ser Phe Asn Trp Pro Lys
        435                 440                 445

Ala Met Pro Pro Lys Glu Gln Glu Asn Tyr Ile Gln Arg Leu Gly Glu
    450                 455                 460

Ile Gly Tyr Val Trp Gln Phe Ile Thr Leu Ala Gly Leu His Thr Asn
465                 470                 475                 480

Ala Leu Ala Ile Asp Asn Phe Ser Arg Glu Phe Ser Arg Phe Gly Met
                485                 490                 495

Arg Ala Tyr Ala Gln Gly Ile Gln Gln Arg Glu Met Asp Glu Gly Val
            500                 505                 510
```

```
Asp Val Leu Lys His Gln Lys Trp Ala Gly Ala Glu Tyr Val Asp Ser
        515                 520                 525

Ile Leu Lys Leu Ala Gln Gly Gly Val Ser Ser Thr Ala Ser Met Gly
        530                 535             540

Lys Gly Val Thr Glu Glu Gln Phe Gly Ser Ser Asn Gly Ala Lys Leu
545                 550                 555                 560
```